United States Patent [19]

Weck et al.

[11] Patent Number: 5,460,718

[45] Date of Patent: Oct. 24, 1995

[54] DOMESTIC WATER TREATING DEVICE INCLUDING PERMANENT MAGNET MEANS

[75] Inventors: David Weck, Miami Beach; Erwin M. Frey, Fort Lauderdale; Fred J. Meyer, North Miami Beach, all of Fla.

[73] Assignee: Micasa Trading Corporation, Miami, Fla.

[21] Appl. No.: 225,276

[22] Filed: Apr. 8, 1994

[51] Int. Cl.⁶ .................................. C02F 1/48; C02F 1/50
[52] U.S. Cl. .......................... 210/205; 210/222; 4/22.75; 261/DIG. 46; 422/186.02; 422/266
[58] Field of Search ........................ 210/205, 206, 210/222, 223; 4/227.5; 422/22, 23, 266, 275, 186.01, 186.02; 261/DIG. 46

[56] References Cited

U.S. PATENT DOCUMENTS 4,157,963  6/1979  Jessop et al. .................... 261/DIG. 46
4,416,854  11/1983  Nielsen .................................. 422/266
4,954,263  9/1990  Woodhouse ............................ 210/222

Primary Examiner—Matthew O. Savage
Attorney, Agent, or Firm—Lowe, Price, LeBlanc & Becker

[57]   ABSTRACT

A water treating device for a domestic water handling device such as a toilet water tank, an air conditioning drain pan or a humidifier includes a housing having permanent magnets in a flow path of water flowing through the housing via openings in the housing, to collect free ions in the water. An antimicrobial polymer disinfecting agent is in a mass inserted in a chamber in the housing and/or in a polymer in a housing surface. The housing is configured so an air bubble forms against the housing roof to assure that a base of the housing rests on the floor of the water handling device. Ribs adding structural strength to the cover are aligned and have approximately the same size and shape as slots in the cover roof through which water passes so the ribs obscure the magnets from view from above and to sides of the cover. The magnets are held in place by a spring finger extending upward from the base to exert a force downwardly against the magnet upper pole face.

27 Claims, 3 Drawing Sheets

DOMESTIC WATER TREATING DEVICE INCLUDING PERMANENT MAGNET MEANS

FIELD OF THE INVENTION

The present invention relates generally to domestic water treating devices and more particularly to a domestic water treating device including permanent magnets for precipitating metal ions tending to discolor and/or adversely affect the operation of domestic water handling devices, such as toilets, humidifiers and air conditioning pans.

BACKGROUND ART

Magnets have been used in industrial and domestic liquid handling devices to precipitate free ions as anion and cations on opposite polarity pole faces of the magnets. A domestic water treating device using permanent magnets has been commercialized for use in toilet tanks, air conditioner pans and humidifiers to minimize or prevent discoloration of toilet bowls and buildup of deposits on parts. Domestic water treating devices using permanent magnets have advantages over chemical devices designed to remove stains from toilet tanks because the permanent magnets have a much greater effective life than chemicals and do not require addition of a coloring agent.

The commercial device generally includes a plastic base carrying two flat permanent magnets and a plastic cover that frictionally fits on the base to assist in holding the magnets in place relative to transverse and longitudinal center planes, about which the device is symmetrical. The base includes downwardly depending feet, designed to space the base exterior floor from a floor of the water containing structure into which the water treating device is to be placed. The magnets are held in place by studs projecting upwardly from an interior floor of the base and by posts downwardly depending from an interior roof of the cover. A liquid flow path between the interior of the water treating device and the aqueous body in which it is located is provided by holes in the base and roof of the cover, as well as large windows in side walls of the cover which enable the permanent magnets to be easily seen. In addition, a flow path is provided between the interior of the device and the aqueous body via openings provided between ears which extend from the base along the longitudinal center plane and contact side walls of the cover.

While the described prior art device has been commercialized, it has not been particularly commercially successful. When the prior art permanent magnet device is released base down from the surface of the aqueous body, to descend to the floor of a container for the aqueous body, the device falls in a random manner and finally comes to rest on the container floor on its roof and base with approximately equal probability. This is frequently perceived as being an improper position for the device by the home dweller who then feels he/she must insert his/her hand into the tank and place the device in an upright position with its base down. Many home dwellers regard this as a rather unpleasant exercise.

The prior art device also has the disadvantage, from a commercial standpoint, of being somewhat unsightly. The large windows contribute to this unsightliness and give the appearance of a rather flimsy structure having poor craftsmanship.

From an operational standpoint, there is a relatively high flow impedance path between the base interior floor and the bottom magnet pole faces adjacent or abutting that floor. This is because there is a negligible or zero gap between the bottom pole faces and the base interior floor. Because of the high impedance flow path to the bottom pole face, there is a reduction in the number of anion or cations precipitated from the water to the bottom pole face to reduce the efficiency of the device in preventing stains and buildup of minerals on the water handling device in which the water treating device is located.

Another disadvantage of the prior art device is that it functions only to precipitate anions and cations. Many homeowners are desirous, for one reason or another, of removing bacteria from toilet bowl water, as well as water droplets circulated via forced air heating and cooling circulation systems including humidifiers and air conditioners. It is also desirable for bacteria neutralizing, removing or killing structure used in domestic water treating devices to be longlasting.

It is, accordingly, an object of the present invention to provide a new and improved domestic water treating device, particularly adapted for use with water handling devices such as toilet tanks, air conditioners and humidifiers.

Another object of the present invention is to provide a new and improved domestic water treating device using magnets for reducing buildup of minerals in water handling devices such as toilets, air conditioners and humidifiers.

A further object of the invention is to provide a new and improved domestic water treating device for preventing stains and mineral buildup, as well as to reduce bacteria count, in domestic water handling devices such as toilet bowls and tanks, humidifiers and air conditioners.

An additional object of the invention is to provide a new and improved domestic water treating device having a very long effective life for precipitating minerals and removing bacteria from water in devices such as toilets, air conditioners and humidifiers.

Still an additional object of the invention is to provide a new and improved domestic water treating device including permanent magnets, which device is attractive because, inter alia, the magnets are concealed from view, even though a low impedance flow path is provided to both pole faces of magnets in the device.

Still a further object of the invention is to provide a new and improved domestic water treating device including permanent magnets, which device is arranged so that it always lands with its base against the floor of a water container in which the device is placed, after the device descends base first from the surface of the water to the floor of the water container.

Disclosure of the Invention.

In accordance with one aspect of the present invention, some of the foregoing objects are achieved by a domestic water treating device for a domestic water handling device such as a toilet water tank, a domestic air conditioning drain pan or a domestic humidifier, wherein the water treating device comprises a housing having a size and shape enabling it to be inserted into a water containing portion of the domestic water handling device. The housing includes openings positioned and arranged for enabling water to flow between the water containing portion and the housing. Permanent magnet means in the housing in a flow path of water flowing through the housing via the openings collects free ions in water contacting the magnet means. This aspect of the invention is characterized by providing the housing with a disinfecting agent for neutralizing bacteria in water flowing in the housing. Preferably the disinfecting agent includes an antimicrobial polymer in a mass inserted in a chamber in the housing and/or in a polymer forming an exterior surface of the housing. The permanent magnet means and the disinfecting agent are preferably arranged so there is enhanced flow of water molecules including free ions through the region where the disinfecting agent is located. Bacteria in these free ions containing molecules thus have a tendency to be acted on by the bacterial agent.

Another aspect of the invention is characterized by configuring (1) the base so one of the openings is therein and spaced from a floor of the water containing portion of the domestic water handling device on which the base rests and (2) the housing so the base is assured of resting on the floor when the housing is placed on the top surface of water in the domestic water handling device and thence descends freely to the floor. To achieve this result the housing is preferably configured so an air bubble forms therein against a surface of the housing removed from the base as the housing descends to the floor and the air bubble remains against the surface while the base rests on the floor.

A further aspect of the invention is characterized by providing the cover with (1) some of the openings through which the water flows and (2) a structure positioned relative to said some openings and the magnet means for obscuring the magnet means from view from above and to sides of the cover. This result is preferably attained by arranging the openings in the cover as slots in a roof of the cover and forming the structure obscuring the magnet means as ribs arranged to add structural strength to the cover, wherein each of the slots and ribs is aligned and has approximately the same size and shape.

A further aspect of the invention is concerned with a structure for holding the magnet means in place. This structure includes a spring finger extending upward from an interior floor of the base and having an elongated portion engaging a flat first pole face of the magnet means remote from the interior floor. The spring finger exerts a force downwardly against the remote pole face. A pair of structural strength providing rails on the interior floor extend in a direction approximately at right angles to the elongated direction of the elongated portion of the finger so the elongated portion is partially superposed over one of the rails. The magnet means has a flat second pole face abutting and supported by the rails so there is a gap between the second pole face and the interior floor so a relatively low flow impedance path for water in the housing is provided in the gap. The structure for holding the magnet means in place preferably includes multiple projecting stops extending upwardly from the interior floor, wherein the stops engage side wall portions of the magnet means. The base preferably includes a ramp abutting one of the rails and having an incline direction transverse to the direction of extent of the rails. The ramp is inclined from the interior floor toward a top surface of the rail inside an open end of the finger. The base preferably includes aperture means directly below the second magnet pole face.

A specific aspect of the invention relates to a domestic water treating apparatus for a domestic water handling device such as a toilet water tank, a domestic air conditioning drain pan or a domestic humidifier comprising a housing having a size and shape enabling it to be inserted into a water containing portion of the domestic water handling device. The housing includes transverse and longitudinal center planes having a central intersection and is approximately symmetrical in size and weight about the center planes. The housing includes a unitary molded cover frictionally fit to a unitary molded base. The base includes opposed interior and exterior floors and the cover includes a roof having holes therein so water can flow between the water containing portion of the domestic water handling device and the housing interior. Each of a pair of permanent magnet holding compartments in the base on opposite sides of the transverse center plane of the housing hold a flat permanent magnet so a first substantially planar pole face of the magnets is adjacent the interior floor and a second substantially planar pole face thereof parallel to the first pole face is remote from the interior floor. Each of the holding compartments includes a structure for holding one of the magnets in situ and for positioning a substantial portion of the first pole face away from the base interior floor so a relatively low impedance flow path for water in the housing is provided adjacent a substantial portion of the first pole face. The another pole face is arranged so a substantial portion thereof is freely exposed to water in the housing. A structure extending downwardly from the exterior floor engages a floor of the water containing portion and spaces the exterior floor from the floor of the water containing portion so there is a relatively low impedance flow path for water in the water containing portion between the floor of the water containing portion and below the exterior floor and from the exterior floor into the interior of the housing via openings in the base. The cover includes a pair of walls within the housing and depending downwardly from the roof on opposite sides of the transverse center plane. All of the cover roof holes are between the walls. Each wall and a portion of the cover beyond the wall relative to the transverse center line forms a compartment in which an air bubble is formed as the housing descends base first in the water containing portion. The housing has a center of gravity approximately at the intersection of said planes below the bubbles so the floor engaging structure rests on the floor of the water containing portion.

The base preferably includes a central compartment having wall means extending upwardly from the interior floor. A solid disinfecting agent is located in the central compartment directly above another aperture in the base. The cover has a structural reinforcing rib having finger means extending downwardly into the compartment exerting a downward force on the solid disinfecting agent in the compartment.

The above and still further objects, features and advantages of the present invention will become apparent upon consideration of the following detailed description of a specific embodiment thereof, especially when taken in conjunction with the accompanying drawings.

DESCRIPTION OF THE PREFERRED EMBODIMENT

Figure 1:
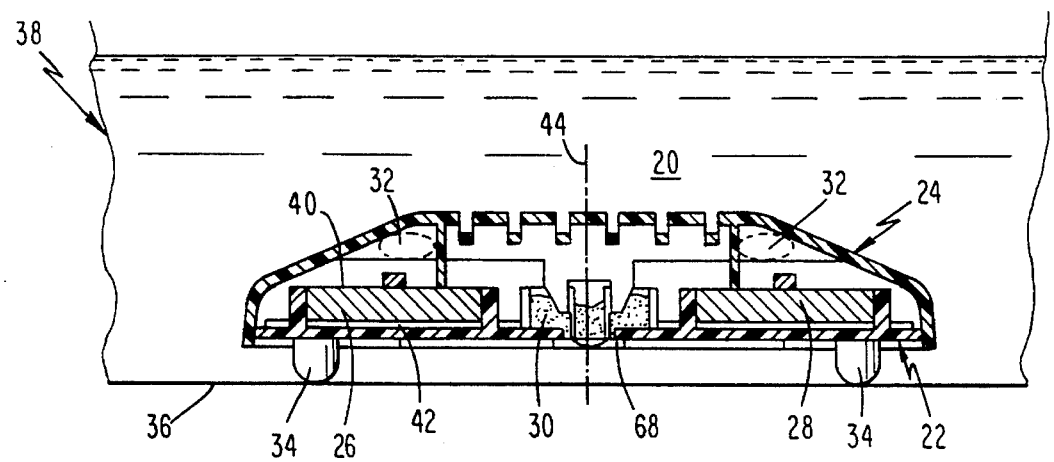
FIG. 1 is a side sectional view of a water treating device in accordance with a preferred embodiment of the present invention in place on a toilet tank floor.
Figure 2:
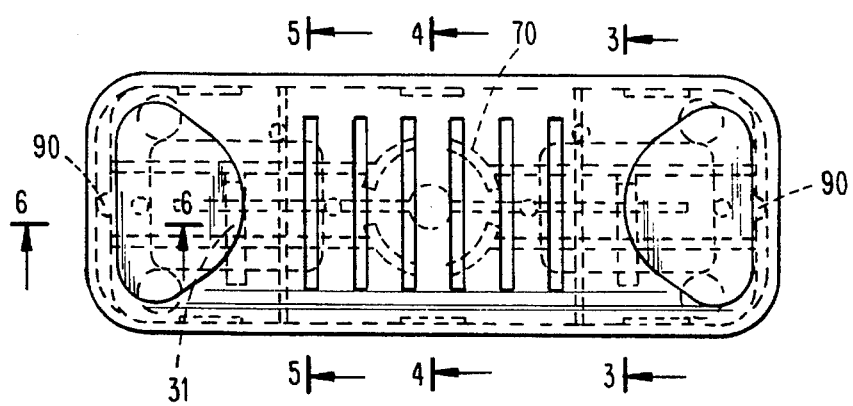
FIG. 2 is a top view of the device illustrated in FIG. 1, with some hidden parts being shown in phantom.
Figure 3:
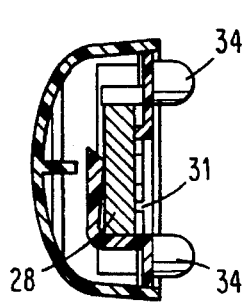
FIG. 3 is a side sectional view, taken through the lines 3—3 of FIG. 2.
Figure 4:
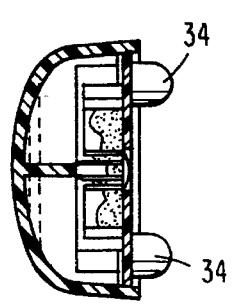
FIG. 4 is a side sectional view taken through the lines 4—4 of FIG. 2, which view is taken along the device transverse center plane.
Figure 5:
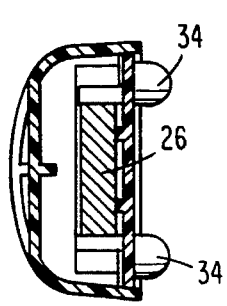
FIG. 5 is a side sectional view taken through the lines 5—5 of FIG. 2.

Reference is now made to FIG. 1 of the drawing wherein housing 20 for the water treating device in accordance with the preferred embodiment of the present invention is illustrated as including base 22 and cover 24, both of which are unitary, plastic thermosetting or thermoplastic molded structures, preferably formed of polypropylene, a rigid, non-magnetic material. Base 22 and cover 24 can contain a color pigment or be white, as long as they are made of a non-magnetic material which can be a non-magnetic metal, although plastics are preferred. Base 22 and cover 24 are held together only by a friction fit between them. In a preferred embodiment, housing 20 is approximately 1½" wide, 4 inches long and ¾" high, so it has a size and shape enabling it to be easily inserted in a domestic water handling device, such as a toilet tank, an air conditioning pan or a humidifier.

Fixedly mounted in base 22 are permanent magnets 26 and 28, as well as disinfecting mass 30 that can be formed as a bunch of fibers or a pellet. Base 22 and cover 24 are constructed so water from the domestic water handling device in which housing 20 is placed flows around and in contact with both pole faces of permanent magnets 26 and 28 and disinfecting mass 30. Housing 20 is constructed so air bubbles 32 form against the upper interior wall of cover 24 when housing 20 is released, base first, at the water surface of the domestic water handling device. Bubbles 32 cause housing 20 to invariably land with its feet 34 against the floor of the domestic water handling device, such as floor 36 of toilet tank 38. Because housing 20 is always in an upright position with feet 34 thereof against floor 36, the flow of water from tank 38 around magnets 26 and 28 and disinfectant mass 30 is assured.

Each of permanent magnets 26 and 28 is a flat ferrite body having opposed planar pole faces 40 and 42, such that like polarity pole faces of the magnets are similarly directed relative to base 22, to maximize the magnetic field along vertical transverse center plane 44, about which the magnets are symmetrical and where disinfectant mass 30 is located. Because like polarity pole faces of magnets 26 and 28 are similarly directed relative to base 22, e.g. the north pole faces of magnets 26 and 28, both point upwardly away from base 22, magnetic flux lines from these pole faces are additive where the flux lines pass through disinfectant mass 30. Hence, there is a tendency for free ions in the water flowing through housing 20 to flow against disinfectant mass 30 so bacteria therein tend to be killed to a greater extent than otherwise.

Permanent magnets 26 and 28 also attract and precipitate metal ions, particularly iron, manganese and calcium from the water in tank 38 that flows through housing 20. Free ions (in addition to those of calcium, magnesium and iron) which are in solution in the water are attracted and precipitated as anions and cations to the north and south pole faces of magnets 26 and 28. By removing and precipitating these ions, discoloration of the toilet tank and toilet bowl is extensively reduced. Precipitating these ions from water in humidifiers and air conditioners reduces the mineral buildup on parts of such water handling devices. By providing two magnets in spaced relationship, the magnetism of the magnets tends to be maintained for a long period of time, such as many years. While magnets 26 and 28 are preferably ferrite bodies, it is to be understood that other types of long lasting permanent magnets can be employed.

Disinfectant fiber mass or pellet 30 is preferably a commercially available self-sanitizing antimicrobial plastic product, in fiber or pellet form, made of polyethylene or other thermoplastic material, e.g. acrylics, cellulosic ionomers and polypropylene with a hexachlorophene antimicrobial surface agent or other suitable polymer and an organic antimicrobial surface agent. Commercially available is a complex material dispersed in any of several plastic vehicles to form a colloidal suspension in the plastic vehicle. The colloidal suspension apparently migrates to the surface of the plastic vehicle in submicron particle size. The resulting polymer matrix acts as a constant sentry to replenish the surface to provide continuous antimicrobial capability. Fibers, such as cotton, can be blended with the antimicrobial fibers to provide a wicking action onto the natural fibers. The structure is extremely long lasting and has been found to have no measurable deterioration of antimicrobial capacity in polyethylene during 12 years of shelf life. The antibacterial disinfectant mass 30 neutralizes and kills water borne bacteria in the water flowing through housing 20 which is particularly useful in forced air humidifier and air conditioning applications. It also has the advantage of reducing bacteria from toilet tanks and bowls so there is reduced exposure to bacteria for persons cleaning toilet bowls.

In the commercially available form of disinfectant mass 30, special additives are incorporated into raw plastic before the plastic is molded or extruded into a final product. The additives are evenly mixed throughout the entire plastic body. There is only a small amount of the additive on the surface of the fiber or pellet at any time. This very small amount of additive on the surface kills bacteria, mold and fungus in the water contacting the surface. As the surface additive is removed by friction caused by the water moving across the surface of mass 30, additional additive from inside the plastic carrier moves out to the surface of the plastic, being available to kill additional pathogens. The additive kills germs causing molecular breakdown, odor, mold and mildew that cannot grow on the plastic. This ability to kill pathogens should continue for many years.

The combination of long lasting antibacterial plastic mass 30 and long lasting permanent magnets 26 and 28 enables the water treating structure in housing 20 to have an effective life of many years. Thereby, effective bacterial removal and ion precipitation are provided for many years, resulting in an inexpensive device that is effective for a prolonged time to (1) prevent staining of toilet tanks and toilet bowls and clogging of domestic humidifiers and air conditioners and (2) purify the air circulated by humidifiers and air conditioners for many years. The combination of these two agents in a single inexpensive housing is particularly advantageous to home dwellers.

Base 22 and cover 24 are secured to each other by a frictional fit, to minimize manufacturing labor and material costs. In addition, magnets 26 and 28 and disinfecting mass 30 are frictionally held in place and easily inserted into housing 20, where they are firmly secured. Housing 24 is made so there are low liquid flow impedance paths past both pole faces of magnets 26 and 28 as well as disinfecting mass 30 to provide ample water flow past the pole faces and disinfecting mass.

Cover 24 is constructed so magnets 26 and 28 are obstructed from view from the top and sides of housing 20. Obscuring magnets 26 and 28 from view is particularly advantageous for sales purposes because some consumers would prefer not to see the magnets at the time of purchase and installation of the device included in housing 20.

Housing 20 includes transverse, vertically extending center plane 44 and longitudinally extending center plane 46. The structure of housing 20 is symmetrical about both of center planes 44 and 46 and the center of gravity of the device is below air bubbles 32 at the intersection of the planes, so housing 20 sinks uniformly into the water pool in tank 38 and always lands upright, as illustrated.

Along center plane 46, cover 24 has a generally trapezoidal shape including planar roof 48 including six transverse slots 50. Aligned with each of slots 50 is a transverse rib 52 which provides structural transverse support for the cover, while obscuring magnets 26 and 28 and disinfecting mass 30 from the view of a viewer looking down on roof 48 and from the sides of cover 24.

Downwardly depending from roof 48 into the interior of housing 20 and beyond all of slots 50 are parallel transverse walls 54 that extend completely between the lengthwise sides 56 of cover 24. Internal walls 54 function as structural reinforcing ribs and cooperate with external, sloping walls 58 of cover 24 to form closed compartments 60 where bubbles 32 are formed as housing 20 descends feet first into the water of toilet tank 38. Bubbles 32 are formed in compartments 60 because the air between walls 54 and 58 is trapped in the closed compartments and cannot escape from the compartments as housing 20 descends in tank 38. Bubbles 32 provide buoyancy for the top portion of housing 20, to assure that roof 48 is always up and feet 34 are always down, against floor 36, after housing 20 is released base down from the top water surface of tank 38.

Reinforcing rib 62 extends longitudinally, along center plane 46, so it is connected to the upper portion of side wall segment 58 and depends downwardly from roof 48. Reinforcing rib 62 includes downwardly depending fingers 64, symmetrically located about transverse center plane 44; notch 66 is provided between fingers 64. Disinfecting mass 30, whether in fiber or pellet form, is held in place by fingers 64, which press against the fibers or against the top of the pellet, to compress the fibers or pellet against the upper, interior face of base 22 in the center portion of housing 20, between magnets 26 and 28. Water flow through disinfectant 30 is provided by a flow path through central, circular opening 68 in base 22 and by the openings provided by slots 50 in roof 48. Disinfectant mass 30 is also held in place by the walls of segmented ring 70, having a center line coincident with the center line of hole 68, at the intersection of planes 42 and 44. Ring 44 is divided into four equi-angular segments to provide gaps to increase the water flow through disinfectant mass 30.

Extending lengthwise along each of side walls 56 at the bottom of cover 24 are three stub ledges 72 which assist in providing a frictional fit for base 22 and cover 24. Each of ledges 72 has an upper face 86 which supports the exterior bottom face 84 of base 22.

Base 22 includes planar upper platform 80 including central circular opening 68 and the segments of ring 70. Platform 80 includes peripheral wall 82 having the same shape and size as the periphery of the bottom of the interior wall of cover 24 so there is a snug fit of edge 82 against the cover interior wall. To prevent excess upward movement of platform 80, walls 54 of cover 24 include downwardly depending segments 88, having bottom edges slightly above or in contact with the upper face of platform 84.

Feet 34, one of which is located close to each corner of platform 80, depend downwardly from the bottom face of the platform. Feet 34 are sufficiently long to provide a low impedance flow path for water flowing between tank floor 36 and the bottom exterior floor of base 22 and through openings in the bottom of base 22 to enhance water flow past the pole faces of magnets 26 and 28, as well as disinfectant mass 30.

Figure 6:
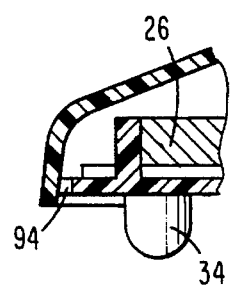
FIG. 6 is a partial sectional view taken through the lines 6—6 of FIG. 2.
Figure 7:
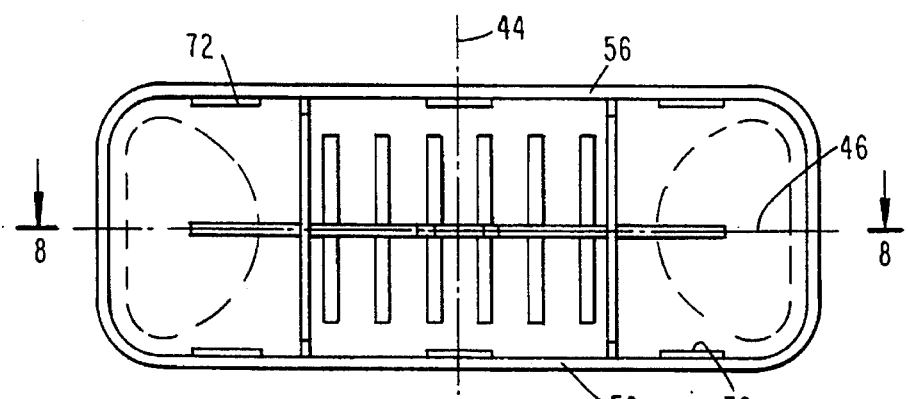
FIG. 7 is a bottom view of a cover included in the device illustrated in FIGS. 1–6.
Figure 8:
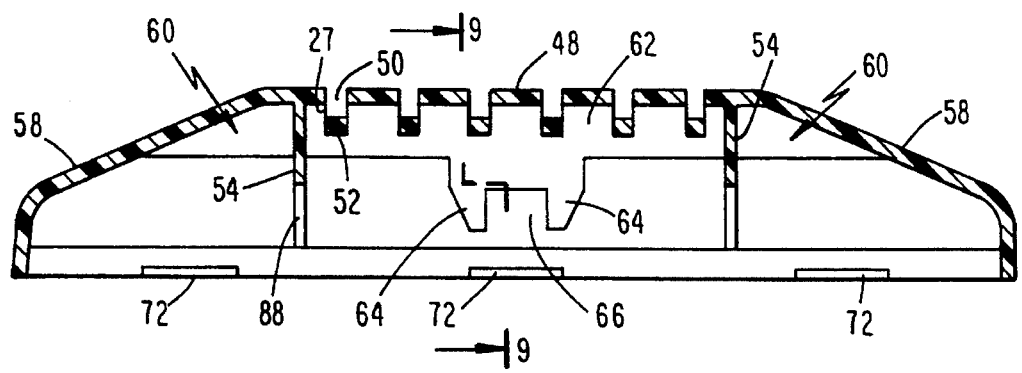
FIG. 8 is a side sectional view taken through the lines 8—8 of FIG. 7.
Figure 9:
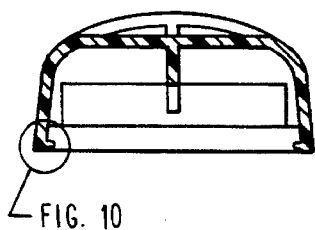
FIG. 9 is a side view taken through the lines 9—9 of FIG. 8.
Figure 10:
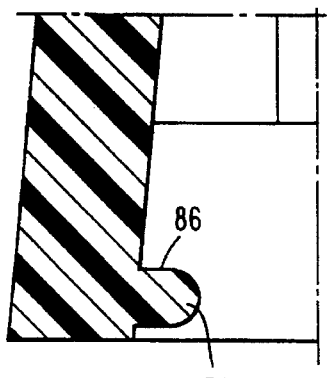
FIG. 10 is a detailed, enlarged view of the portion of FIG. 9 indicated by circular line 10—10.
Figure 11:
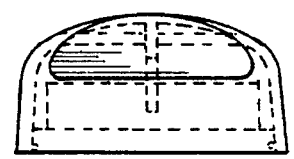
FIG. 11 is a side view of the cover of FIG. 7.
Figure 14:
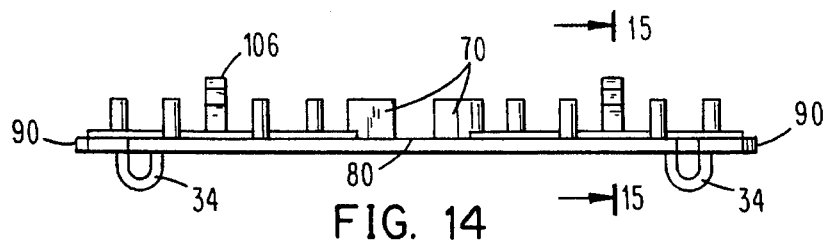
FIG. 14 is a side view of the base illustrated in FIG. 12.
Figure 12:
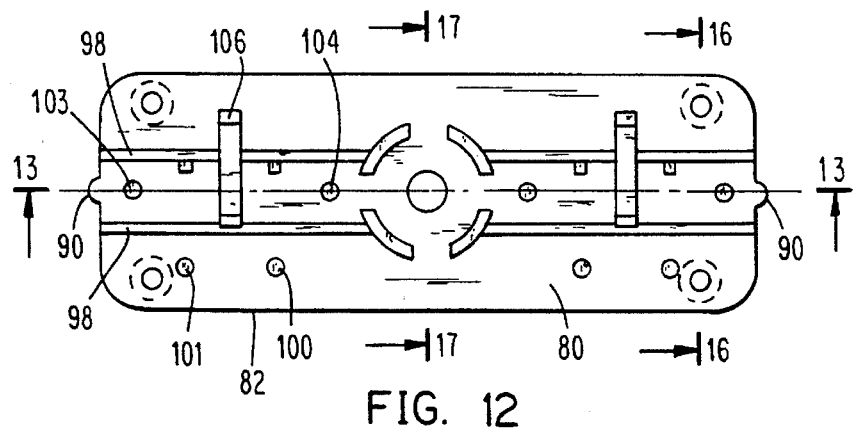
FIG. 12 is a top view of a base included in the device illustrated in FIGS. 1–7.
Figure 13:
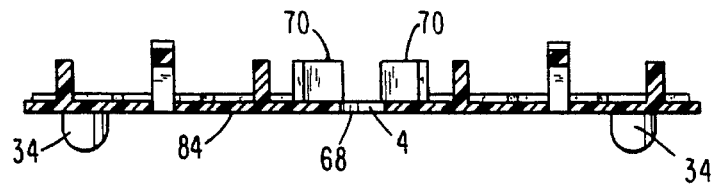
FIG. 13 is a longitudinal sectional view taken through the lines 13—13 of FIG. 12.
Figure 15:
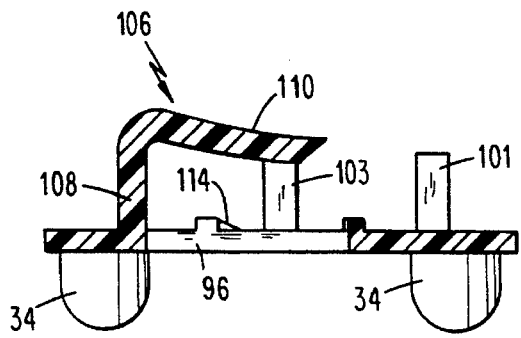
FIG. 15 is a side sectional view taken through the lines 15—15 of FIG. 14.
Figure 16:
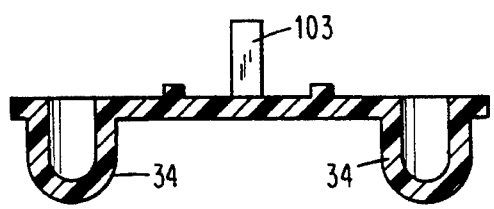
FIG. 16 is a side sectional view taken through the lines 16—16 of FIG. 12.
Figure 17:
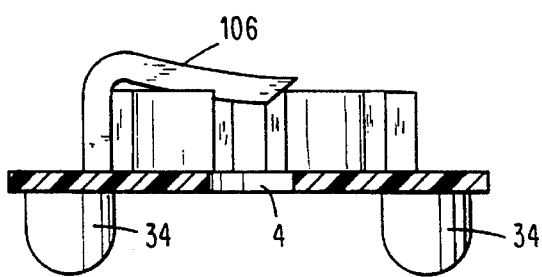
FIG. 17 is a side sectional view taken through the center transverse line 17—17 of FIG. 12.

Ears 90 project outwardly from the side walls of platform 80, along longitudinal cross sectional plane 42 to provide a standoff for the portion of cover 22 immediately adjacent thereto. Thereby, water flows in the direction of plane 46 through gap 94, FIG. 6, between tank 38 and the interior of housing 20, around both pole faces of magnets 26 and 28. Water flow between tank 38 and the interior of housing 20 in the vicinity of magnets 26 and 28 is also provided by transversely extending slots 96, each of which is directly below the center portions of the lower pole faces of magnets 26 and 28. The water flowing through gaps 94 and slots 96 flows around magnets 26 and 28 and a central compartment between walls 54 and through the openings defined by slots 50 and the volume above ribs 52. A portion of the water flowing through gaps 94 and slots 96 also flows through the gaps between the segments of ring 70 into contact with disinfectant fiber mass 30. Thereby, such water is subjected to the action of permanent magnets 26 and 28, to remove metal ions, and the disinfectant action of mass 30, to remove bacteria. Permanent magnets 26 and 28 have like polarity pole faces arranged so magnetic field lines from the pole faces are additive where disinfectant fiber mass 30 is located. Thereby, disinfectant fiber mass 30 is positioned where the magnetic field from permanent magnets 26 and 28 is maximized.

The flow path impedance past the lower pole faces of magnets 26 and 28 is reduced by mounting the magnets on longitudinally extending, parallel rails 98 which are symmetrically located relative to center planes 42 and 44 and have a height of about ⅛". Thereby, the bottom faces of magnets 26 and 28 are spaced from the upper surface of platform 80. The flow of water through openings 68, gaps 94 and slots 96 is also enhanced by the approximately ¼" spacing of the bottom face of platform 80 away from tank floor 36 provided by feet 34.

Each of magnets 26 and 28, both having a generally rectangular shape with rounded edges, is held in place on rails 98 by upwardly extending pegs 100–104 and spring 106. Spring 106 has an upwardly extending leg 108 that is mounted on platform 80. Extending in a generally horizontal but slightly downward direction from leg 108 is finger 110 that is generally aligned with transversely extending slot 96. Finger 110 has a horizontal extent from leg 108 slightly beyond the center line between rails 98 so it hangs over slot 96. Pegs 100–104 have a height approximately equal to the height of magnets 26 and 28 so tops of the pegs are approximately coplanar with the top faces of the magnets. When no magnet is inserted between pegs 100–104, finger 110 extends slightly below the top edges of pegs 100–104. Pegs 100 and 101 are positioned in front of the opening between finger 110 and platform 80, while pegs 103 and 104 are positioned on longitudinal center plane 42. The side walls of magnets 26 and 28 abut against vertically extending walls of pegs 100–104 and vertically extending leg 108 of finger 106, while the top of finger 110 presses down on the upper planar pole face of the magnets.

To facilitate insertion of magnets 26 and 28, back ramps 114 extend from the back rail 98 below finger 110 toward center plane 46. Each of ramps 114 is about equidistant from the side walls of the magnet which is above it and is inclined about 45° relative to the interior floor of base 22.

During manufacture, magnets 26 and 28 are sideways slipped under pegs 100 and 101, with transverse and lateral movement of the magnets being prevented by pegs 100–104. Then, disinfecting mass 30 is positioned between the interior surfaces of ring 70. Base 22, with magnets 26 and 28 and disinfecting mass 30 located thereon, is then inserted through the bottom of cover 24 and held in place by ledges 72 against the lower part of ribs 21. Longitudinal movement of base 22 relative to cover 24 is prevented by the side walls of ears 90 on platform 80 engaging the interior, downwardly depending lower side wall portions of cover 24. Transverse movement of base 22 relative to cover 24 is prevented by the base side edges bearing against lower interior side wall portions of cover 24.

While there has been described and illustrated one specific embodiment of the invention, it will be clear that variations in the details of the embodiment specifically illustrated and described may be made without departing from the true spirit and scope of the invention as defined in the appended claims. For example, the antibacterial agent included in disinfectant mass 30 can be also included in the thermoplastic material forming base 22 and cover 24 to increase the amount of antibacterial agent available. Alternatively, the antibacterial agent in base 22 and cover 24 can be a substitute for the antibacterial mass 30.

We claim:

1. A domestic water treating apparatus for a domestic water handling device such as a toilet water tank, a domestic air conditioning drain pan or a domestic humidifier; the apparatus comprising:

a housing having a size and shape enabling it to be inserted into a water containing portion of the domestic water handling device, the housing including openings positioned and arranged for enabling water to flow between the water containing portion and the housing;

permanent magnet means in the housing in a flow path of water flowing through the housing via the openings for collecting free ions in water contacting the magnet means;

the housing including a disinfecting agent for neutralizing bacteria in water flowing in the housing, the disinfecting agent including an organic antimicrobial surface agent in a plastic vehicle, whereby said antimicrobial surface agent forms a colloidal suspension with said vehicle that migrates to a surface of the vehicle.

2. The domestic water treating apparatus of claim 1 wherein the disinfecting agent is in a mass inserted in a chamber in the housing.

3. The domestic water treating apparatus of claim 1 wherein the disinfecting agent is included in a polymer forming an exterior surface of the housing.

4. The domestic water treating apparatus of claim 1 wherein the housing includes a base on which the magnet means is secured and a cover secured to the base, the cover including some of said openings above a polarized face of the magnetic means when the apparatus is properly in place in the water handling device, and a structure under said openings when the apparatus is properly in place in the water handling device, the structure being positioned so the magnet means is obscured from view from above and to all sides of the cover.

5. The domestic water treating apparatus of claim 4 wherein said some openings in the cover include slots and the structure under said openings when the apparatus is properly in place in the water handling device includes ribs arranged to add structural strength to the cover, each of said slots and ribs being aligned and having approximately the same size and shape.

6. The domestic water treating apparatus of claim 1 wherein the disinfectant agent is positioned where the magnet field from the magnet means is maximized.

7. The domestic water treating apparatus of claim 1 wherein the magnet means includes first and second like polarity permanent magnet pole faces arranged so magnetic field lines from the pole faces are additive in a region the disinfectant agent is located.

8. A domestic water treating apparatus for a domestic water handling device such as a toilet water tank, a domestic air conditioning drain pan or a domestic humidifier; the apparatus comprising:

a housing having a size and shape enabling it to be inserted into a water containing portion of the domestic water handling device, the housing including openings positioned and arranged for enabling water to flow between the water containing portion and the housing;

permanent magnet means in the housing in a flow path of water flowing through the housing via the openings for collecting free ions in water contacting the magnet means;.

the housing including a disinfecting agent for neutralizing bacteria in water flowing in the housing, the housing including a base configured so one of said openings is therein and spaced from a floor of the water containing portion of the domestic water handling device on which the base rests, the housing being configured so (a) said base is assured of resting on the floor when the housing is placed on the top surface of water in the domestic water handling device and thence descends freely to the floor and (b) water contacts a substantial portion of both polarized faces of each permanent magnet of the magnet means.

9. The domestic water treating apparatus of claim 8 wherein the housing is configured so an air bubble forms therein against a surface of the housing removed from the base as the housing descends to the floor and the air bubble remains against the surface while the base rests on the floor.

10. A domestic water treating apparatus for a domestic water handling device such as a toilet water tank, a domestic air conditioning drain pan or a domestic humidifier; the apparatus comprising:

a housing having a size and shade enabling it to be inserted into a water containing portion of the domestic water handling device, the housing including openings positioned and arranged for enabling water to flow between the water containing portion and the housing;

permanent magnet means in the housing in a flow path of water flowing through the housing via the openings for collecting free ions in water contacting the magnet means;

the housing including a disinfecting agent for neutralizing bacteria in water flowing in the housing, the housing including a base having one of said openings therein and a cover having some of the openings therein, the cover being secured to the base, said permanent magnet means including a pair of flat permanent magnets secured to the base so they are on opposite sides of a common transverse center plane of the base and cover and substantial portions of both pole faces of each magnet are contacting water in the housing, the pole faces being generally parallel to an interior floor of the base, the base having an exterior floor having downwardly depending feet for contacting a floor of the water containing portion of the domestic water handling device and for spacing the opening in the base from the floor of the water containing portion of the domestic water handling device, a chamber formed on the base interior floor on the center plane, the disinfecting agent being included in a plastic mass including an antimicrobial polymer, the mass being held in place in said chamber, a pair of compartments being formed in the cover for trapping air that forms air bubbles as the housing freely descends in the water containing portion of the domestic water handling device, the compartment being defined by a pair of walls downwardly depending from a roof of the cover and ending slightly above top pole faces of said magnets when the apparatus is properly in place in the water handling device, each of the magnets being held in place by a spring finger extending upwardly from the interior floor of the base and engaging the upper polarized face of each magnet when the apparatus is properly in place in the water handling device.

11. A domestic water treating apparatus for a domestic water handling device such as a toilet water tank, a domestic air conditioning drain pan or a domestic humidifier, the apparatus comprising:

a housing having a size and shape enabling it to be inserted into a water containing portion of the domestic water handling device, the housing including transverse and longitudinal center planes having a central intersection, the housing being approximately symmetrical in size and weight about the center planes;

the housing including a unitary molded cover frictionally fit to a unitary molded base, the base including opposed interior and exterior floors, the cover including a roof having holes therein so water can flow between the water containing portion of the domestic water handling device and the housing interior, a pair of permanent magnet holding compartments in the base on opposite sides of the transverse center plane of the housing, a flat permanent magnet in each of the magnet holding compartments positioned so a first substantially planar pole face thereof is adjacent the interior floor and a second substantially planar pole face thereof parallel to the first pole face is remote from the interior floor, each of the holding compartments including a structure for holding one of the magnets in situ and for positioning a substantial portion of said first pole face away from the base interior floor so a relatively low impedance flow path for water in the housing is provided adjacent a substantial portion of said first pole face, the second pole face being arranged so a substantial portion thereof is freely exposed to water in the housing when the apparatus is properly in place in the water handling device, a structure extending downwardly from the exterior floor when the apparatus is properly in place in the water handling device for engaging a floor of the water containing portion and for spacing the exterior floor from the floor of the water containing portion so there is a relatively low impedance flow path for water in the water containing portion between the floor of the water containing portion and below the exterior floor when the apparatus is properly in place in the water handling device and from the exterior floor into the interior of the housing via openings in the base, the cover including a pair of walls within the housing and depending downwardly when the apparatus is properly in place in the water handling device from the roof on opposite sides of the transverse center plane, all of said cover roof holes being between the walls, each wall and a portion of the cover beyond the wall relative to the transverse center line forming a compartment in which an air bubble is formed as the housing descends base first in the water containing portion, the housing having a center of gravity approximately at the intersection of said planes below the bubbles so the floor engaging structure rests on the floor of the water containing portion.

12. The domestic water treating apparatus of claim 11 wherein the structure for holding each magnet in place includes a spring finger extending upwardly from the interior floor engaging the another pole face of the magnet when the apparatus is properly in place in the water handling device, the spring finger exerting a force downwardly against the another pole face.

13. The domestic water treating apparatus of claim 12 wherein the structure for holding each magnet in place includes multiple projecting stops extending upwardly from the interior floor when the apparatus is properly in place in the water handling device, the stops engaging side wall portions of each magnet.

14. The domestic water treating apparatus of claim 13 wherein the structure for positioning a substantial portion of said one pole face away from the base interior floor includes a pair of longitudinally extending structural reinforcement rails on the base interior floor, a ramp abutting one of said rails and having an incline direction transverse to the longitudinal axis and being inclined from the interior floor toward the top of a rail inside an open end of the finger when the apparatus is properly in place in the water handling device; the finger, stops and ramp being arranged so the magnet can be slid into place in the direction of the upward incline of the ramp below the finger.

15. The domestic water treating apparatus of claim 11 wherein the openings in the base include apertures directly below the another face of each magnet when the apparatus is properly in place in the water handling device.

16. The domestic water treating apparatus of claim 15 wherein the base includes a central compartment having wall means extending upwardly from the interior floor when the apparatus is properly in place in the water handling device, a solid disinfecting agent in the central compartment, the openings including another aperture in the base directly under the central compartment when the apparatus is properly in place in the water handling device, the cover having a structural reinforcing rib having finger means extending downwardly into the compartment exerting a downward force on the solid disinfecting agent in the compartment.

17. The domestic water treating apparatus of claim 16 wherein the base includes ears for pushing side walls of the cover away from the base to provide gaps between the side walls and base through which water from the water containing portion can flow into the housing.

18. The domestic water treating apparatus of claim 17 wherein the cover includes a structure positioned relative to said openings and said magnets so said magnets are obscured from view from above and to sides of the cover when the apparatus is properly in place in the water handling device.

19. The domestic water treating apparatus of claim 18 wherein the openings in the roof cover include slots and the magnet obscuring structure, the cover including some of said openings and the structure positioned relative to said some openings and said magnet means for obscuring the magnet means from view from above and to sides of the cover when the apparatus is properly in place in the water handling device.

20. The domestic water treating apparatus of claim 11 wherein the base includes a central compartment having wall means extending upwardly from the interior floor, a solid disinfecting agent in the central compartment, the openings including an aperture in the base directly under the central compartment, the cover having a structural reinforcing rib having finger means extending downwardly into the compartment exerting a downward force on the solid disinfecting agent in the compartment when the apparatus is properly in place in the water handling device.

21. A domestic water treating apparatus for a domestic water handling device such as a toilet water tank, a domestic air conditioning drain pan or a domestic humidifier; the apparatus comprising:

a housing having a size and shape enabling it to be inserted into a water containing portion of the domestic water handling device, the housing including openings positioned and arranged for enabling water from the water containing portion to flow through the housing;

permanent magnet means in the housing in a flow path of water flowing through the housing via the openings for collecting free ions in water contacting the magnet;

the housing including a base configured so one of said openings is therein and spaced from a floor of the water containing portion of the domestic water handling device on which the base rests;

the housing being configured so said base is assured of resting on the floor when the housing is placed on the top surface of water in the domestic water handling device and thence descends freely to the floor regardless of the depth of water in the domestic water handling device and water contacts a substantial portion of all polarized faces of the magnet means.

22. The domestic water treating apparatus of claim 21 wherein the housing is configured so an air bubble forms therein against a surface of the housing removed from the base as the housing descends to the floor and the air bubble remains against the surface while the base rests on the floor.

23. A domestic water treating apparatus for a domestic water handling device such as a toilet water tank, a domestic air conditioning drain pan or a domestic humidifier, the apparatus comprising:

a housing having a size and shape enabling it to be inserted into a water containing portion of the domestic water handling device, the housing including openings positioned and arranged for enabling water from the water containing portion to flow through the housing, permanent magnet means in the housing in a flow path of water flowing through the housing via the openings for collecting free ions in water contacting the magnet means, the housing including a base on which the magnet means is secured and a cover secured to the base, the cover including some of said openings and a structure positioned relative to said some openings and said magnet means for obscuring the magnet means from view from above and to sides of the cover regardless of the depth of water in the domestic water handling device, the openings in the cover including slots in a roof of the cover, the structure obscuring the magnet means including ribs arranged to add structural strength to the cover, each of said slots and ribs being aligned and having approximately the same size and shape.

24. A domestic water treating apparatus for a domestic water handling device such as a toilet water tank, a domestic air conditioning drain pan or a domestic humidifier, the apparatus comprising:

a housing having a size and shape enabling it to be inserted into a water containing portion of the domestic water handling device, the housing including openings positioned and arranged for enabling water from the water containing portion to flow through the housing, permanent magnet means in the housing in a flow path of water flowing through the housing via the openings for collecting free ions in water contacting the magnet means, the housing including a base on which the magnet means is secured and a cover secured to the base, a structure for holding the magnet means in place including a spring finger extending upward from an interior floor of the base and having an elongated portion engaging a flat first pole face of the magnet means remote from the interior floor, the spring finger exerting a force downwardly against the remote pole face when the apparatus is properly in place in the water handling device, a pair of structural strength providing rails on the interior floor extending in a direction approximately at right angles to the elongated direction of the elongated portion of the finger so the elongated portion is superposed over one of said rails, the magnet means having a flat second pole face abutting and being supported by the rails so there is a gap between the second pole face and the interior floor so a relatively low flow impedance path for water in the housing is provided in the gap.

25. The domestic water treating apparatus of claim 24 wherein the structure for holding magnet means in place includes multiple projecting stops extending upwardly from the interior floor when the apparatus is properly in place in the water handling device, the stops engaging side wall portions of the magnet means.

26. The domestic water treating apparatus of claim 25 wherein the base includes a ramp abutting one of said rails having an incline direction transverse the direction of extent of the rails and being inclined from the interior floor toward a top surface of the rail inside an open end of the finger when the apparatus is properly in place in the water handling device, wherein the structure for holding each magnet of the magnet means in place includes multiple projecting stops extending upwardly from the interior floor when the apparatus is properly in place in the water handling device, the stops engaging side wall portions of each magnet.

27. The domestic water treating apparatus of claim 26 wherein the base includes aperture means directly below the second magnet pole face.

* * * * *